United States Patent
Hartley et al.

(10) Patent No.: US 10,130,812 B2
(45) Date of Patent: Nov. 20, 2018

(54) CONNECTORIZED COCHLEAR IMPLANT SYSTEMS AND METHODS

(71) Applicant: ADVANCED BIONICS AG, Staefa (CH)

(72) Inventors: Lee F. Hartley, Carlsbad, CA (US); Lakshmi N. Mishra, Carlsbad, CA (US)

(73) Assignee: Advanced Bionics AG, Staefa (CH)

( * ) Notice: Subject to any disclaimer, the term of this patent is extended or adjusted under 35 U.S.C. 154(b) by 12 days.

(21) Appl. No.: 15/408,261

(22) Filed: Jan. 17, 2017

(65) Prior Publication Data
US 2017/0120051 A1    May 4, 2017

Related U.S. Application Data

(62) Division of application No. 14/424,419, filed as application No. PCT/US2012/052718 on Aug. 28, 2012, now Pat. No. 9,555,242.

(51) Int. Cl.
*A61N 1/36* (2006.01)
*A61N 1/05* (2006.01)
(Continued)

(52) U.S. Cl.
CPC ....... *A61N 1/36032* (2013.01); *A61N 1/0541* (2013.01); *A61N 1/3787* (2013.01);
(Continued)

(58) Field of Classification Search
CPC .............. A61N 1/36032; A61N 1/0541; A61N 1/36103; A61N 1/08; A61N 1/3605;
(Continued)

(56) References Cited

U.S. PATENT DOCUMENTS 6,272,382 B1   8/2001   Faltys et al.
7,054,691 B1   5/2006   Kuzma et al.
(Continued)

FOREIGN PATENT DOCUMENTS

CN   101081188 A   12/2007
CN   101926693 A   12/2010
(Continued)

OTHER PUBLICATIONS

International Search Report and Written Opinion received in International Application No. PCT/US12/052718, dated May 24, 2013.
(Continued)

*Primary Examiner* — Deborah Malamud
(74) *Attorney, Agent, or Firm* — ALG Intellectual Property, LLC

(57) ABSTRACT

An exemplary method includes cochlear implant circuitry, which is disposed within a cochlear implant module configured to be implanted within a patient, performing the following: 1) detecting that an implantable antenna is connected to a modular connector coupled to the cochlear implant module, 2) operating in accordance with a radio frequency ("RF") inductive link communication protocol while the implantable antenna is connected to the modular connector, 3) detecting a disconnection of the implantable antenna from the modular connector and a connection of an implantable sound processor to the modular connector, and 4) dynamically switching from operating in accordance with the RF inductive link communication protocol to operating in accordance with a hard wired baseband link communication protocol in response to the connection of the implantable sound processor to the modular connector.

20 Claims, 6 Drawing Sheets

(51) Int. Cl.
*A61N 1/372* (2006.01)
*A61N 1/378* (2006.01)
*H04R 25/00* (2006.01)

(52) U.S. Cl.
CPC ....... *A61N 1/37217* (2013.01); *H04R 25/554* (2013.01); *H04R 25/556* (2013.01)

(58) Field of Classification Search
CPC ............ A61N 1/37217; A61N 1/37229; A61N 1/375; A61N 1/05; A61N 1/36125; A61N 1/372; A61N 1/37252; A61N 1/00; A61N 1/36; A61N 1/3752; H04R 2225/67; G06F 3/015; A61F 2002/183; A61F 2/18; A61M 2210/0662; H01R 2201/12; A61B 5/486; A61B 5/686; A61B 5/4047; A61B 5/6803; A61B 5/04001
See application file for complete search history.

(56) References Cited

U.S. PATENT DOCUMENTS

| | | | |
|---|---|---|---|
| 7,349,618 | B2 | 3/2008 | Nielsen et al. |
| 2003/0229381 | A1 | 12/2003 | Hochmair et al. |
| 2006/0183965 | A1 | 8/2006 | Kasic, II et al. |
| 2010/0198303 | A1 | 8/2010 | Haller et al. |
| 2010/0292758 | A1 | 11/2010 | Lee et al. |
| 2011/0144719 | A1 | 6/2011 | Perkins et al. |
| 2011/0152976 | A1 | 6/2011 | Perkins et al. |
| 2011/0295331 | A1 | 12/2011 | Wells et al. |
| 2012/0197374 | A1 | 8/2012 | Vogt et al. |
| 2015/0290458 | A1 | 10/2015 | Hartley et al. |

FOREIGN PATENT DOCUMENTS

| | | |
|---|---|---|
| CN | 102640435 A | 8/2012 |
| CN | 104582788 A | 4/2015 |
| WO | WO-2010/028436 | 3/2010 |
| WO | WO-2010/088549 | 8/2010 |
| WO | WO-2012/106205 | 8/2012 |

OTHER PUBLICATIONS

International Search Report and Written Opinion received in International Application No. PCT/US13/052929, dated Sep. 16, 2013.
Communication pursuant to Article 94(3) EPC received in European Patent Application No. 12 756 060.5, dated Feb. 12, 2016.
First Office Action received in Chinese Patent Application No. 201380045209.3, dated Dec. 25, 2015.
Communication pursuant to Article 94(3) EPC received in European Patent Application No. 13745990.5, dated Jan. 29, 2016.
First Office Action received in Chinese Patent Application No. 201280075472.2, dated Jan. 15, 2016.
Non-Final Office Action received in U.S. Appl. No. 14/424,419 dated Jun. 13, 2016.
Second Office Action received in Chinese Patent Application No. 201380045209.3, dated Aug. 29, 2016.
Second Office Action received in Chinese Patent Application No. 201280075472.2, dated Sep. 14, 2016.
Non-Final Office Action received in U.S. Appl. No. 14/424,420 dated Jan. 23, 2017.

CONNECTORIZED COCHLEAR IMPLANT SYSTEMS AND METHODS

RELATED APPLICATIONS

The present application is a divisional application of U.S. patent application Ser. No. 14/424,419, filed Feb. 26, 2015 and issued as U.S. Pat. No. 9,555,242, which application is a U.S. National Stage Entry of PCT Application No. PCT/US2012/052718, filed Aug. 28, 2012. These applications are incorporated herein by reference in their respective entireties.

BACKGROUND INFORMATION

Conventional cochlear implant systems include various components configured to be implanted within a patient (e.g., a cochlear implant, an antenna, and an electrode lead) and various components configured to be located external to the patient (e.g., a sound processor, a battery, and a microphone). Unfortunately, the external components of a conventional cochlear implant system are often relatively large, bulky, and aesthetically unpleasing. Hence, various fully implantable cochlear implant systems have been described in which the sound processor and one or more other components typically located external to the patient (i.e., the battery and/or the microphone) are also implanted within the patient. In these configurations, the patient may enjoy cochlear implant functionality with little or no externally located components for various periods throughout the day.

Unfortunately, some patients cannot initially be fitted with a fully implantable cochlear implant system. For example, some patients (e.g., pediatric patients) may possess one or more physiological traits that may limit the number and/or size of components that may be implanted within their heads. Other patients may be unable to be fitted with a fully implantable cochlear implant system for technological, logistical, and/or financial reasons. Hence, these patients may be initially fitted with a conventional cochlear implant system. However, over time, they may become eligible for a fully implantable cochlear implant system. Such an upgrade would typically require a patient to undergo a surgical procedure in which all of the already implanted components of the conventional cochlear implant system are replaced with the new fully implantable cochlear implant system components. In addition to being invasive and costly, this surgical procedure could potentially cause damage to one or more of the patient's auditory structures and thereby negate any benefits that could be provided by the fully implantable cochlear implant system.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
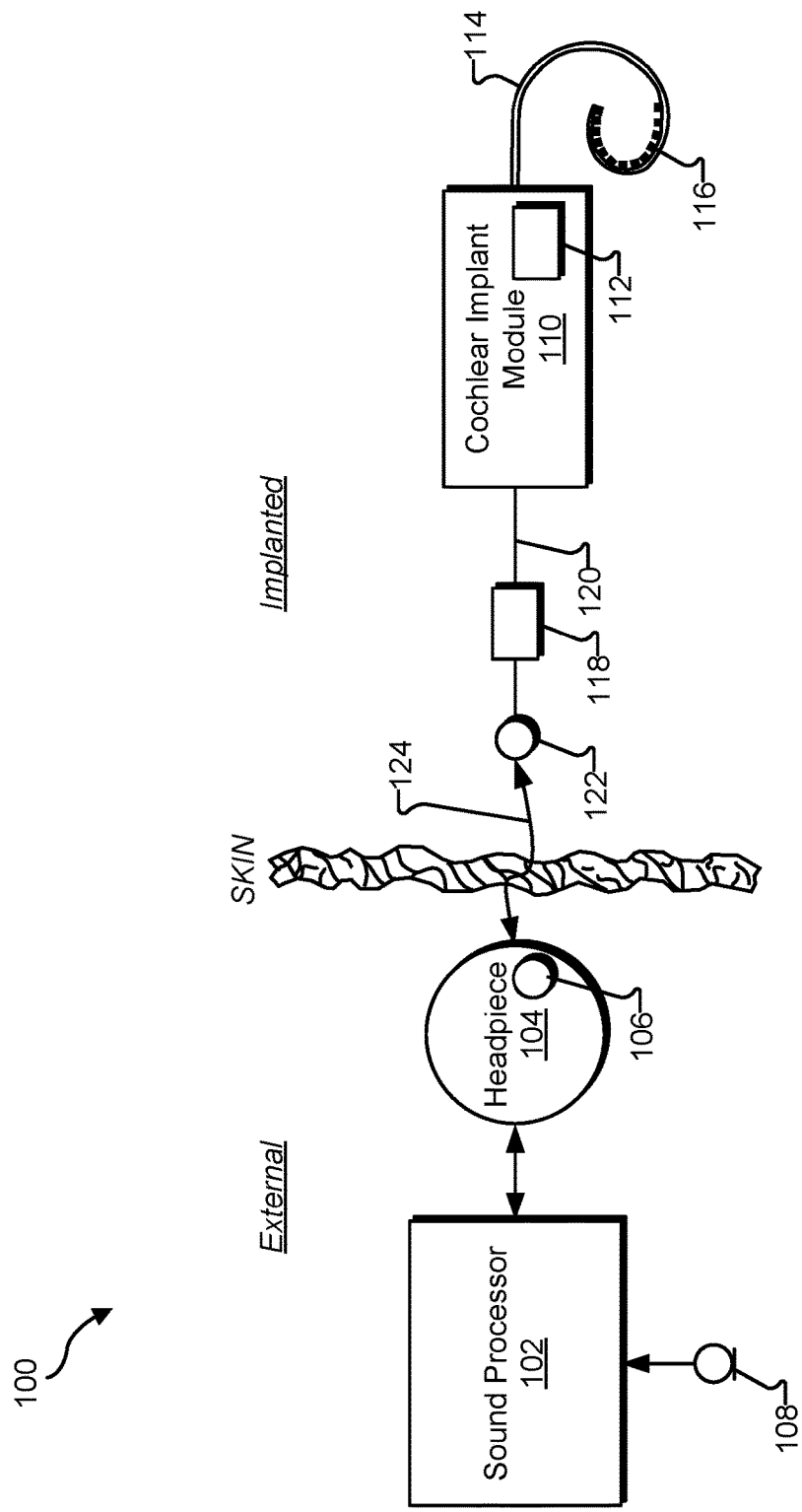
FIG. 1 illustrates an exemplary connectorized cochlear implant system according to principles described herein.

Connectorized cochlear implant systems and methods are described herein. As will be described in more detail below, a connectorized cochlear implant system may include 1) a cochlear implant module configured to be implanted within a patient and comprising cochlear implant circuitry configured to apply electrical stimulation representative of one or more audio signals to the patient, and 2) a modular connector coupled to the cochlear implant module by way of a cable and configured to be implanted within the patient. The modular connector may be removably connected to an implantable antenna in order to facilitate communicative coupling of the implantable antenna to the cochlear implant circuitry. In this configuration, the cochlear implant circuitry may wirelessly communicate with a sound processor located external to the patient. The modular connector may alternatively be removably connected to an implantable sound processor. In this configuration, the cochlear implant circuitry and the implantable sound processor may communicate one with another by way of a wired connection.

The systems and methods described herein may facilitate individual replacement of one or more components of a cochlear implant system after they have been implanted within a patient. For example, a patient may be initially fitted with a connectorized cochlear implant system such as those described herein. The modular connector included in the connectorized cochlear implant system may initially be connected to an implantable antenna. In this manner, the cochlear implant circuitry may operate as it normally would in a conventional cochlear implant system (i.e., one in which the cochlear implant circuitry wirelessly communicates with a sound processor located external to the patient). The patient may subsequently desire to upgrade to a fully implantable cochlear implant system configuration. To do so, the patient may undergo a minimally invasive surgical procedure during which the implantable antenna is disconnected from the modular connector, discarded, and replaced with an implantable sound processor (e.g., by connecting the modular connector to the implantable sound processor.) Advantageously, the remaining implanted components (i.e., the cochlear implant module and the electrode lead) may be left intact, thereby preserving their functionality and avoiding the cost and potential dangers associated with replacing them with new components as well.

As another example, another patient may be initially fitted with a connectorized cochlear implant system such as those described herein. In this example, the modular connector included in the connectorized cochlear implant system may initially be connected to an implantable sound processor. Subsequently, it may be necessary to service the sound processor or replace the sound processor with a new sound processor (e.g., if the originally implanted sound processor becomes defective). Because the implanted sound processor may be easily disconnected from the modular connector, such service and/or replacement of the implanted sound processor may be performed without removing the remaining implanted components (i.e., the cochlear implant module and the electrode lead) from the patient.

FIG. 1 illustrates an exemplary connectorized cochlear implant system 100. As shown, connectorized cochlear implant system 100 may include various components configured to be located external to a patient including, but not limited to, a sound processor 102, a headpiece 104, an external antenna 106, and a microphone 108. Connectorized cochlear implant system 100 may further include various components configured to be implanted within the patient including, but not limited to, a cochlear implant module 110, cochlear implant circuitry 112 included within cochlear implant module 110, a lead 114 having a plurality of electrodes 116 disposed thereon, a modular connector 118 disposed at a distal end of a cable 120 coupled to cochlear implant module 110, and an implantable antenna 122. As will be described in more detail below, additional or alternative components may be included within connectorized cochlear implant system 100 as may serve a particular implementation. The components shown in FIG. 1 will now be described in more detail.

Sound processor 102 may be configured to direct cochlear implant circuitry 112 to generate and apply electrical stimulation (also referred to herein as "stimulation current") representative of one or more audio signals (e.g., one or more audio signals detected by microphone 108, input by way of an auxiliary audio input port, etc.) to one or more stimulation sites associated with an auditory pathway (e.g., the auditory nerve) of the patient. Exemplary stimulation sites include, but are not limited to, one or more locations within the cochlea, the cochlear nucleus, the inferior colliculus, and/or any other nuclei in the auditory pathway. To this end, sound processor 102 may process the one or more audio signals in accordance with a selected sound processing strategy or program to generate appropriate stimulation parameters for controlling cochlear implant circuitry 112. Sound processor 102 may include or be implemented by a behind-the-ear ("BTE") unit, a body worn device, an electro-acoustic stimulation ("EAS") device, and/or any other sound processing unit as may serve a particular implementation.

Headpiece 104 may be communicatively coupled to sound processor 102 and may include an external antenna 106 (e.g., a coil and/or one or more wireless communication components) configured to facilitate selective wireless coupling of sound processor 102 to cochlear implant circuitry 112. Headpiece 104 may be additionally or alternatively be used to selectively and wirelessly couple any other external device to cochlear implant circuitry 112. To this end, headpiece 104 may be configured to be affixed to the patient's head and positioned such that external antenna 106 is communicatively coupled to implantable antenna 122 (which may also be implemented by a coil and/or one or more wireless communication components). In this manner, stimulation parameters and/or power signals may be wirelessly transmitted between sound processor 102 and cochlear implant module 110 via a communication link 124 (which may include a bi-directional communication link and/or one or more dedicated uni-directional communication links as may serve a particular implementation).

Cochlear implant module 110 may be implemented by any type of implantable stimulator that may be used in association with the systems and methods described herein. For example, cochlear implant module 110 may be implemented by an implantable cochlear stimulator. In some alternative implementations, cochlear implant module 110 may be implemented by a brainstem implant and/or any other type of cochlear implant that may be implanted within a patient.

In some examples, cochlear implant module 110 may include cochlear implant circuitry 112 disposed therein. In these examples, cochlear implant module 110 may include a hermetic housing or feedthrough case configured to house cochlear implant circuitry 112. Cochlear implant circuitry 112 may be configured to generate electrical stimulation representative of an audio signal processed by sound processor 102 (e.g., an audio signal detected by microphone 108) in accordance with one or more stimulation parameters transmitted thereto by sound processor 102. Cochlear implant circuitry 112 may be further configured to apply the electrical stimulation to one or more stimulation sites within the patient via one or more electrodes 116 disposed along lead 114. In some examples, cochlear implant circuitry 112 may include a plurality of independent current sources each associated with a channel defined by one or more of electrodes 116. In this manner, different stimulation current levels may be applied to multiple stimulation sites simultaneously by way of multiple electrodes 116.

As shown, cochlear implant module 110 may be coupled to both lead 114 and cable 120. Lead 114 and cable 120 may each be coupled to cochlear implant module 110 in any suitable manner. For example, a proximal end of lead 114 may be integrated into or otherwise permanently coupled to cochlear implant module 110 such that the one or more wires disposed within lead 114 and associated with electrodes 116 may pass through cochlear implant module 110 to cochlear implant circuitry 112. Likewise, a proximal end of cable 120 may be integrated into or otherwise permanently coupled to cochlear implant module 110 such that one or more wires disposed within cable 120 may pass through cochlear implant module 110 to cochlear implant circuitry 112.

As shown, modular connector 118 may be coupled to cochlear implant module 110 by way of cable 120. In some examples, cable 120 may include one or more wires disposed therein configured to facilitate electrical connection of one or more corresponding contacts (e.g., pins) included within modular connector 118 to one or more feedthrough connections included in cochlear implant circuitry 110. Alternatively, cable 120 may include one or more optical fibers and/or any other type of data transmission means as may serve a particular implementation. For purposes of the examples described herein, it will be assumed that cable 120 includes one or more wires disposed therein.

Modular connector 118 may be coupled to a distal end of cable 120 in any suitable manner. For example, modular connector 118 may be permanently affixed to the distal end of cable 120 such that a plurality of contacts (e.g., pins) included within modular connector 118 are electrically connected to each of a plurality of wires included within cable 120.

Modular connector 118 may include any type of connector configured to be removably connected to implantable antenna 122 and one or other suitably configured components (e.g., an implantable sound processor). For example, modular connector 118 may include a plug apparatus configured to plug into a corresponding receptacle associated with implantable antenna 122 (or any other suitably configured component such as an implantable sound processor). The receptacle associated with implantable antenna 122 may be integrated into implantable antenna 122, coupled to a distal end of a cable connected to implantable antenna 122, or otherwise associated with implantable antenna 122. As used herein, references to modular connector 118 being "removably connected" to a particular component (e.g., implantable antenna 122 or an implantable sound processor) refer to the modular connector 118 being capable of being relatively easily and/or readily disconnected (e.g., unplugged) from the particular component by a surgeon or other person in a way that does not damage either the modular connector 118 or the particular component.

While implantable antenna 122 is connected to modular connector 118, implantable antenna 122 may be communicatively coupled to cochlear implant circuitry 112. In this configuration, sound processor 102 may communicate with cochlear implant circuitry 112 by wirelessly transmitting data from external antenna 106 to implantable antenna 122.

In some examples, modular connector 118 may be disconnected from implantable antenna 122 and connected to another component (e.g., an implantable sound processor, a replacement antenna for implantable antenna 122, or another suitable component). Disconnection of modular connector 118 from implantable antenna 122 and connection of modular connector 118 to another component may be performed, e.g., by a surgeon during a surgical procedure.

To illustrate, a patient may be initially fitted with connectorized cochlear implant system 100 shown in FIG. 1. Subsequently, the patient may desire to upgrade to a fully implantable cochlear implant system configuration. To this end, modular connector 118 may be disconnected from implantable antenna 122 and connected to an implantable sound processor.

Figure 2:
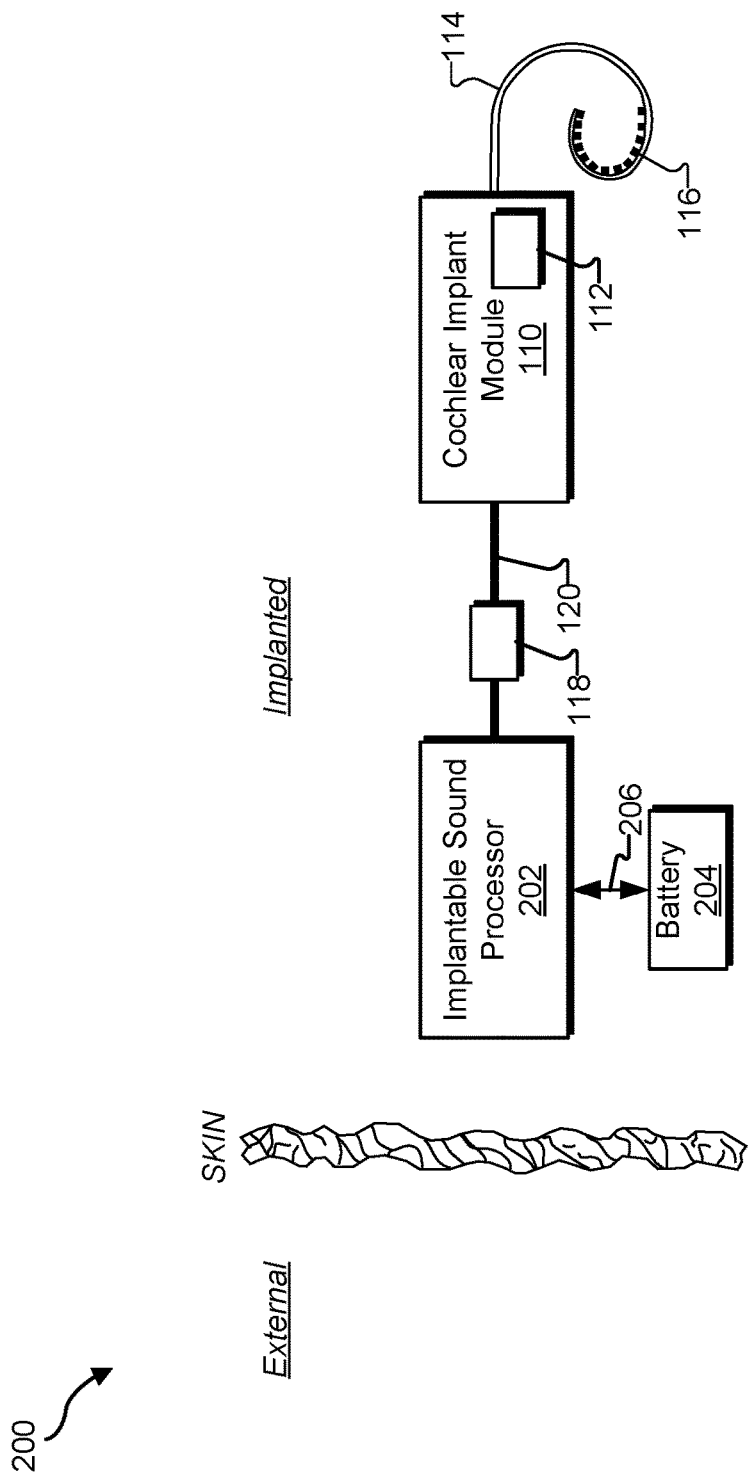
FIGS. 2-5 illustrate exemplary implementations of the connectorized cochlear implant system of FIG. 1 according to principles described herein.

FIG. 2 illustrates an exemplary configuration 200 of connectorized cochlear implant system 100 in which modular connector 118 is removably connected to an implantable sound processor 202 that, together with an implantable battery 204, has been implanted within the patient. Implantable battery 204 may be configured to provide operating power for implantable sound processor 202 and/or one or more other implanted components (e.g., cochlear implant circuitry 112) by way of a communication link 206. In some examples, cochlear implant circuitry 112 may include (or otherwise be associated with) another implantable battery (not shown) configured to provide operating power for cochlear implant circuitry 112. It will be recognized that any of the batteries described herein may be rechargeable or non-rechargeable as may serve a particular implementation.

Implantable sound processor 202 may be architecturally similar to sound processor 102 in that it directs cochlear implant circuitry 112 to generate and apply electrical stimulation representative of one or more audio signals (e.g., one or more audio signals detected by an external or implanted microphone (not shown)) to one or more stimulation sites associated with an auditory pathway (e.g., the auditory nerve) of the patient. However, implantable sound processor 202 may communicate with cochlear implant circuitry 112 by way of a hard wired connection provided by the one or more wires disposed within cable 120.

In some examples, implantable sound processor 202 may include a charging coil configured to facilitate wireless recharging of implantable battery 204 with an external device (e.g., an external charging device). In these examples, the need for implantable antenna 122 in configuration 200 may be obviated. Alternatively, implantable antenna 122 may be configured to serve as a charging antenna for implantable battery 204. To this end, implantable antenna 122 may be connected to implantable sound processor 202 by way of another modular connector.

Figure 3:
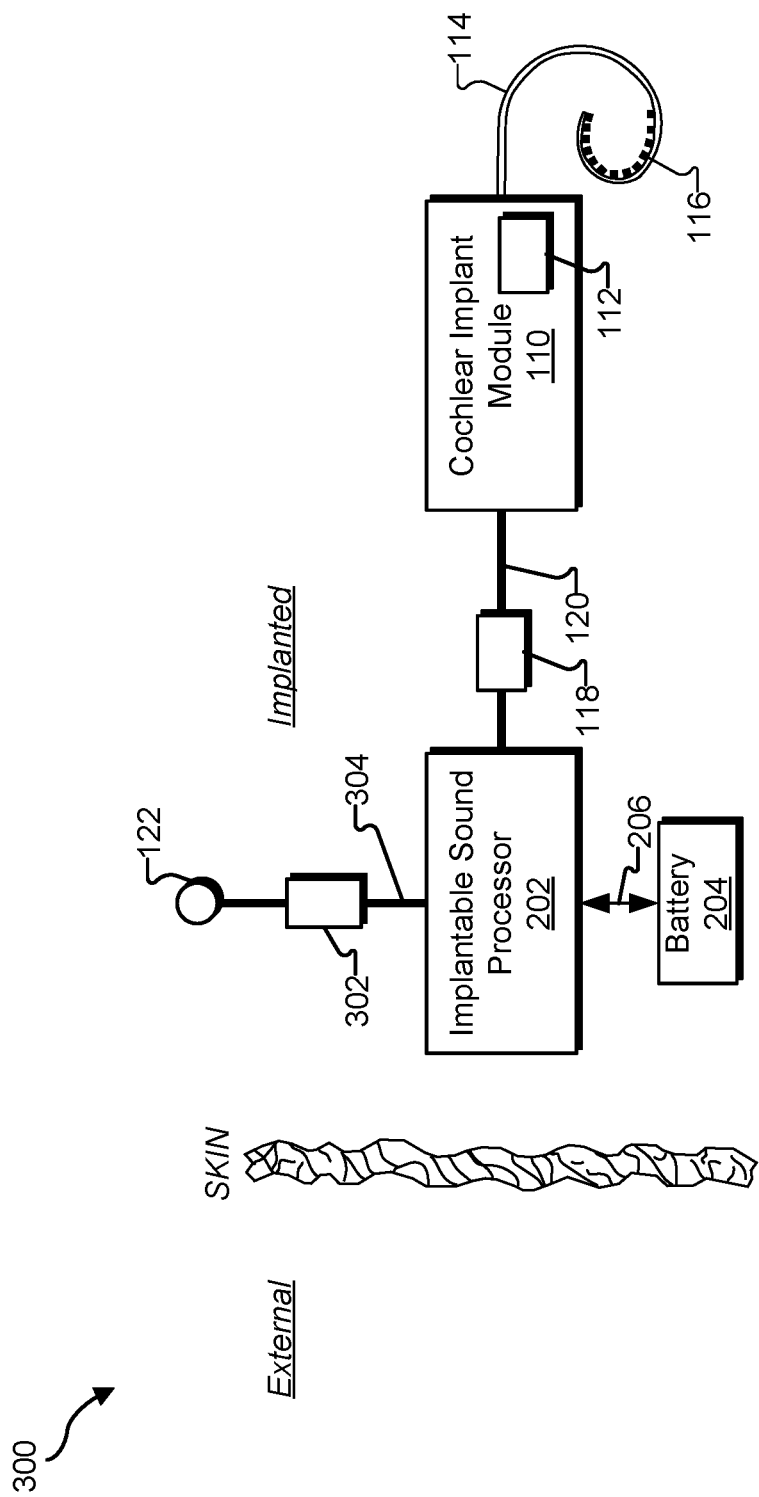

To illustrate, FIG. 3 shows another exemplary configuration 300 of connectorized cochlear implant system 100 wherein implantable antenna 122 is communicatively coupled to implantable sound processor 202 by way of a modular connector 302. Modular connector 302 may be similar to modular connector 118, for example, and may be disposed at a distal end of a cable 304 coupled to implantable sound processor 202.

Returning to FIG. 2, implantable sound processor 202 and implantable battery 204 may be implanted within the patient in any suitable manner and at any suitable location as may serve a particular implementation. For example, as illustrated in FIG. 2, implantable sound processor 202 and implantable battery 204 may implanted as separate units. In this implementation, communication link 206 may be implemented by a cable and/or one or wires interconnecting implantable sound processor 202 and implantable battery 204.

Figure 4:
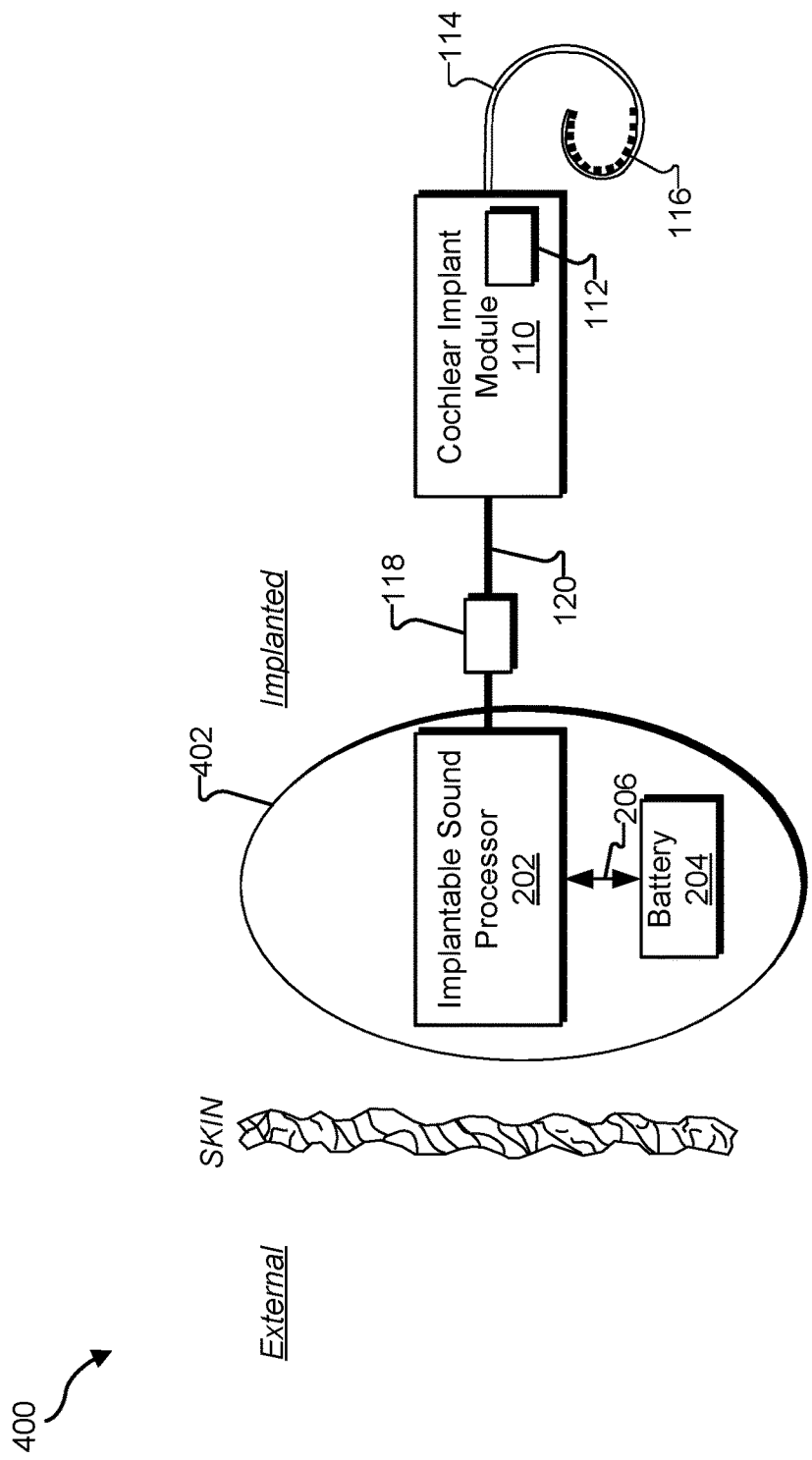

Alternatively, as shown in the exemplary implementation 400 of FIG. 4, implantable sound processor 202 and implantable battery 204 may be housed within a single overmold 402 (or other type of hermetic housing). In this implementation, communication link 206 may be implemented by one or more electric feedthroughs, contacts, or other conductive means.

Figure 5:
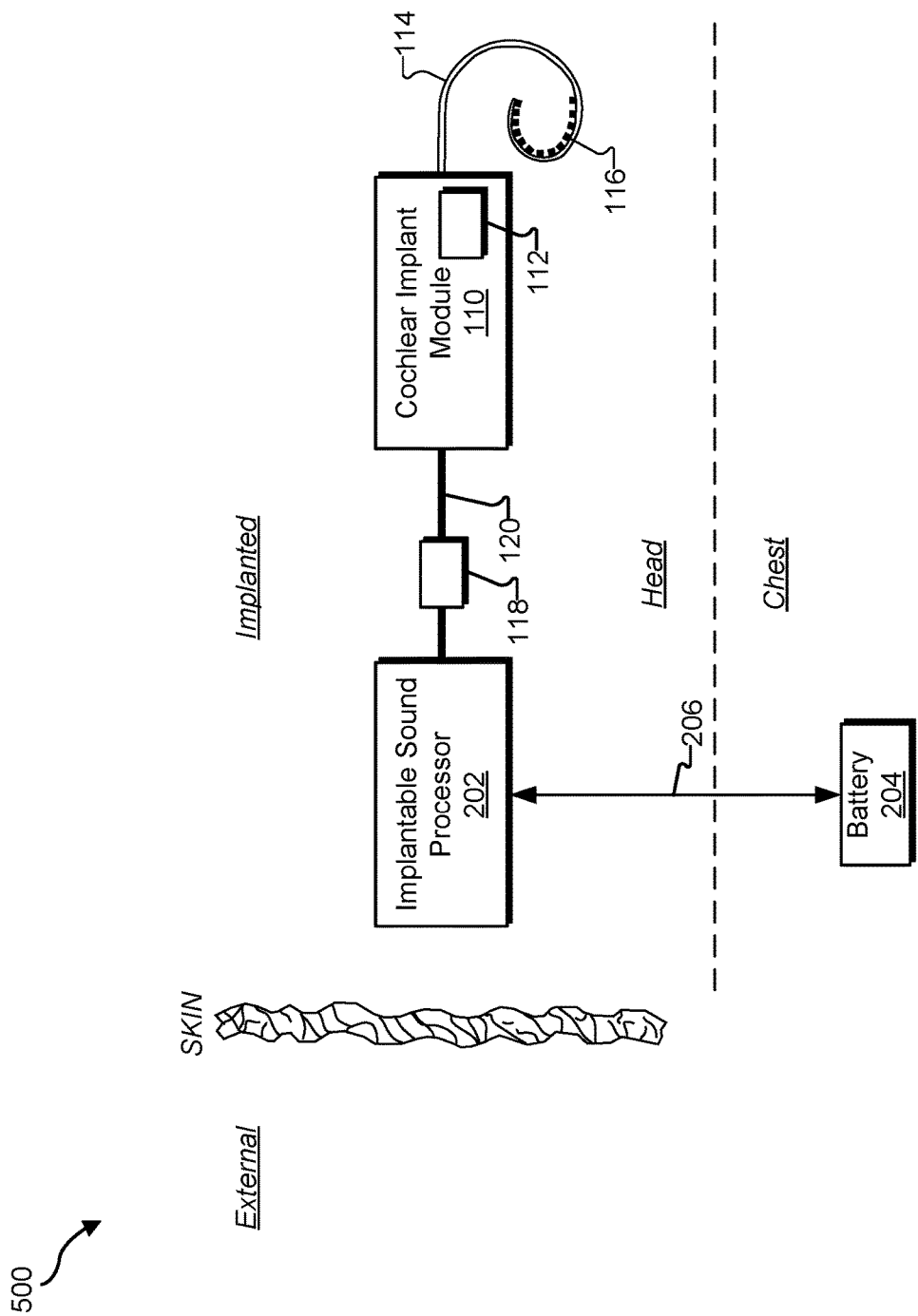

In some examples, both implantable sound processor 202 and implantable battery 204 are implanted within the head of the patient. Alternatively, as shown in the exemplary implementation 500 of FIG. 5, implantable sound processor 202 may be implanted within the head of the patient and implantable battery 204 may be implanted within the chest of the patient (or in any other suitable location capable of being implanted with a relatively large battery). In this case, communication link 206 may be implemented by a cable and/or one or wires tunneled from the chest to the head.

Once implantable sound processor 202 has been implanted, it may be activated (i.e., turned on) in any suitable manner (e.g., by utilizing any of the techniques described in WO 2011/095229 A1, which application is incorporated herein by reference in its entirety) by any suitable activation means. Likewise, implantable sound processor 202 may be deactivated (e.g., to conserve power or for any other reason) using any of the techniques described in WO 2011/095229 A1 or in any other suitable manner.

In some examples, implantable sound processor 202 may be configured to detect a fault in the connection of modular connector 118 to implantable sound processor 202 (e.g., a short or open circuit in the connection). In response, implantable sound processor 202 may initiate a shut down procedure in which implantable sound processor 202 safely shuts down and notifies a user of the connection fault.

In some examples, cochlear implant circuitry 112 may be configured to automatically detect that a particular component is connected to modular connector 118 and operate in accordance with a protocol corresponds to the particular component. For example, cochlear implant circuitry 112 may detect that implantable antenna 122 is connected to modular connector 118, and, in response, operate in accordance with a radio frequency ("RF") inductive link communication protocol while implantable antenna 122 is connected to modular connector 122. As used herein, an "RF inductive link communication protocol" refers to any suitable communication protocol that may be used to wirelessly communicate with an external sound processor (e.g., sound processor 102).

Subsequently, cochlear implant circuitry 112 may detect a disconnection of implantable antenna 122 from modular connector 118 and a connection of implantable sound processor 202 to modular connector 118. In response, cochlear implant circuitry 112 may dynamically switch from operating in accordance with the RF inductive link communication protocol to operating in accordance with a hard wired baseband link communication protocol while implantable sound processor 202 is connected to modular connector 118. As used herein, a "hard wired baseband link communication protocol" refers to any suitable communication protocol that may be used to communicate with an implanted sound processor (e.g., sound processor 202) by way of a wired link.

Cochlear implant circuitry 112 may be configured to automatically detect that a particular component is connected to modular connector 118 in any suitable manner. For example, as described above, modular connector 118 may include a plurality of contacts. Cochlear implant circuitry 112 may be configured to detect that implantable antenna 122 is connected to modular connector 118 by determining that a first predetermined number of contacts included in the plurality of contacts are in communication with a corresponding first number of contacts associated with implantable antenna 122. Likewise, cochlear implant circuitry 112 may be configured to detect that implantable sound processor 202 is connected to modular connector 118 by determining that a second predetermined number of contacts included in the plurality of contacts are in communication with a corresponding second number of contacts associated with implantable sound processor 202.

To illustrate, modular connector 118 may include three pins. Implantable antenna 122 may be configured to make electrical contact with only two of the three pins when connected to modular connector 118. In contrast, implantable sound processor 202 may be configured to make electrical contact with all three pins when connected to modular connector 118. Cochlear implant circuitry 112 may accordingly identify which component is connected to modular connector 118 by identifying how many pins are in electrical contact with the component.

It will be recognized that any of the permanently coupled connections described herein may be connectorized in order to further modularize connectorized cochlear implant system 100. For example, lead 114 may alternatively be coupled to cochlear implant module 110 by way of a modular connector and cable 120 may alternatively be coupled to cochlear implant module 110 by way of a modular connector.

Figure 6:
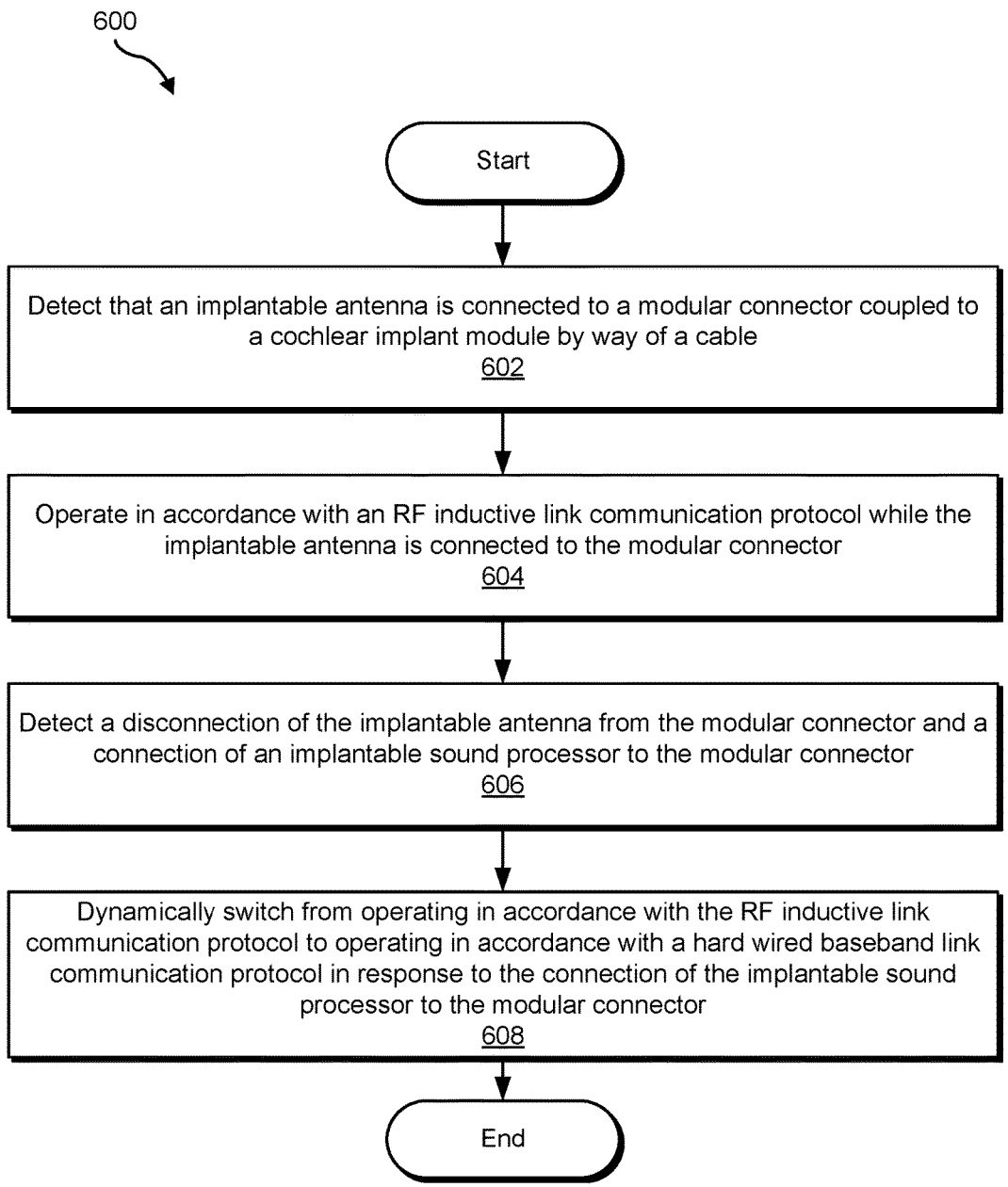
FIG. 6 illustrates an exemplary connectorized cochlear implant method according to principles described herein.

FIG. 6 illustrates an exemplary connectorized cochlear implant method 600. While FIG. 6 illustrates exemplary steps according to one embodiment, other embodiments may omit, add to, reorder, and/or modify any of the steps shown in FIG. 6. One or more of the steps shown in FIG. 6 may be performed by cochlear implant circuitry 112.

In step 602, cochlear implant circuitry detects that an implantable antenna is connected to a modular connector coupled to a cochlear implant module housing the cochlear implant circuitry by way of a cable. Step 602 may be performed in any of the ways described herein.

In step 604, the cochlear implant circuitry operates in accordance with an RF inductive link communication protocol while the implantable antenna is connected to the modular connector. Step 604 may be performed in any of the ways described herein.

In step 606, the cochlear implant circuitry detects a disconnection of the implantable antenna from the modular connector and a connection of an implantable sound processor to the modular connector. Step 606 may be performed in any of the ways described herein.

In step 608, the cochlear implant circuitry dynamically switches from operating in accordance with the RF inductive link communication protocol to operating in accordance with a hard wired baseband link communication protocol in response to the connection of the implantable sound processor to the modular connector. Step 608 may be performed in any of the ways described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A method comprising:
    detecting, by cochlear implant circuitry disposed within a cochlear implant module configured to be implanted within a patient, that an implantable antenna is connected to a modular connector coupled to the cochlear implant module;
    operating, by the cochlear implant circuitry, in accordance with a radio frequency ("RF") inductive link communication protocol while the implantable antenna is connected to the modular connector;
    detecting, by the cochlear implant circuitry, a disconnection of the implantable antenna from the modular connector and a connection of an implantable sound processor to the modular connector; and
    dynamically switching, by the cochlear implant circuitry, from operating in accordance with the RF inductive link communication protocol to operating in accordance with a hard wired baseband link communication protocol in response to the connection of the implantable sound processor to the modular connector.

2. The method of claim 1, wherein:
    the modular connector comprises a plurality of contacts;
    the detecting that the implantable antenna is connected to the modular connector comprises determining that a first predetermined number of contacts included in the plurality of contacts are in communication with a corresponding first number of contacts associated with the implantable antenna; and
    the detecting that the implantable sound processor is connected to the modular connector comprises determining that a second predetermined number of contacts included in the plurality of contacts are in communication with a corresponding second number of contacts associated with the implantable sound processor.

3. The method of claim 1, wherein the modular connector is coupled to the cochlear implant module by way of a cable.

4. The method of claim 3, wherein the modular connector is disposed at a distal end of the cable and the cochlear implant module is coupled to a proximal end of the cable.

5. The method of claim 1, wherein a lead having a plurality of electrodes disposed thereon is permanently coupled to cochlear implant module, and the method further comprises applying, by the cochlear implant circuitry, electrical stimulation to the patient by way of one or more of the electrodes.

6. The method of claim 1, wherein the implantable sound processor is configured to be implanted within a head of the patient.

7. The method of claim 1, wherein an implantable battery configured to be implanted within the patient is communicatively coupled to the implantable sound processor.

8. The method of claim 7, wherein the implantable battery is configured to be implanted within a chest of the patient and communicatively coupled to the implantable sound processor by way of at least one wire.

9. The method of 7, wherein the implantable battery and the implantable sound processor are configured to be housed within a single overmold.

10. A system comprising:
    a cochlear implant module configured to be implanted within a patient and comprising cochlear implant circuitry; and a modular connector coupled to the cochlear implant module and configured to be implanted within the patient;

the cochlear implant circuitry further configured to
- detect that an implantable antenna is connected to the modular connector,
- operate in accordance with a radio frequency ("RF") inductive link communication protocol while the implantable antenna is connected to the modular connector,
- detect a disconnection of the implantable antenna from the modular connector and a connection of an implantable sound processor to the modular connector, and
- dynamically switch from operating in accordance with the RF inductive link communication protocol to operating in accordance with a hard wired baseband link communication protocol in response to the connection of the implantable sound processor to the modular connector.

11. The system of claim 10, wherein the modular connector is configured to facilitate communicative coupling of the implantable antenna to the cochlear implant circuitry while the antenna is connected to the modular connector and communicative coupling of the implantable sound processor to the cochlear implant circuitry while the implantable sound processor is connected to the modular connector.

12. The system of claim 10, wherein:
the modular connector comprises a plurality of contacts;
the cochlear implant circuitry is configured to detect that the implantable antenna is connected to the modular connector by determining that a first predetermined number of contacts included in the plurality of contacts are in communication with a corresponding first number of contacts associated with the implantable antenna; and
the cochlear implant circuitry is configured to detect that the implantable sound processor is connected to the modular connector by determining that a second predetermined number of contacts included in the plurality of contacts are in communication with a corresponding second number of contacts associated with the implantable sound processor.

13. The system of claim 10, wherein the modular connector is coupled to the cochlear implant module by way of a cable.

14. The system of claim 13, wherein the modular connector is disposed at a distal end of the cable and the cochlear implant module is coupled to a proximal end of the cable.

15. The system of claim 10, further comprising a lead having a plurality of electrodes disposed thereon, wherein:
the lead is permanently coupled to cochlear implant module; and
the cochlear implant circuitry is configured to apply electrical stimulation to the patient by way of one or more of the electrodes.

16. The system of claim 10, wherein the implantable sound processor is configured to be implanted within a head of the patient.

17. The system of claim 10, further comprising an implantable battery configured to be implanted within the patient and to be communicatively coupled to the implantable sound processor.

18. The system of claim 17, wherein the implantable battery is configured to be implanted within a chest of the patient and communicatively coupled to the implantable sound processor by way of at least one wire.

19. The system of 17, wherein the implantable battery and the implantable sound processor are configured to be housed within a single overmold.

20. The system of claim 10, wherein the cochlear implant circuitry is configured to communicate with the implantable sound processor while operating in accordance with the hard wired baseband link communication protocol.

* * * * *